United States Patent [19]

Hunter

[11] Patent Number: 5,353,629
[45] Date of Patent: Oct. 11, 1994

[54] SMOKE METER

[75] Inventor: Colin Hunter, Dunstable, England

[73] Assignee: L. L. Churchill Limited, England

[21] Appl. No.: 907,393

[22] Filed: Jul. 1, 1992

[30] Foreign Application Priority Data

Jul. 5, 1991 [GB] United Kingdom ............... 9114588
Sep. 3, 1991 [GB] United Kingdom ............... 9118822

[51] Int. Cl.⁵ .......................................... G01N 21/59
[52] U.S. Cl. ............................... 73/28.01; 73/16; 356/439
[58] Field of Search ............... 73/31.05, 28.01, 1 G; 356/438, 439, 440

[56] References Cited

U.S. PATENT DOCUMENTS

| 1,967,428 | 7/1934 | Quereau | 356/438 |
| 1,969,626 | 8/1934 | Simon et al. | 73/28.01 |
| 3,826,577 | 7/1974 | Irwin | 356/438 |
| 4,544,273 | 10/1985 | Berndt | 356/438 |

FOREIGN PATENT DOCUMENTS

| 0233536 | 11/1985 | Japan | 356/439 |
| 0468136 | 4/1975 | U.S.S.R. | 356/438 |
| 0754266 | 8/1980 | U.S.S.R. | 356/438 |
| 1136064 | 1/1985 | U.S.S.R. | 356/438 |

Primary Examiner—Hezron E. Williams
Assistant Examiner—Michael Brock
Attorney, Agent, or Firm—Basile and Hanlon

[57] ABSTRACT

A smoke meter is particularly adapted to meter the smoke content of vehicle exhaust gases. The meter includes a measuring tube with a light at one end and a light detector at the other end, the amount of light detected corresponding to the smoke content. The optical surfaces are kept clean by inducing a flow of clean air across the surfaces using an air supply which also induces flow of gas into the measuring tube.

7 Claims, 1 Drawing Sheet

}

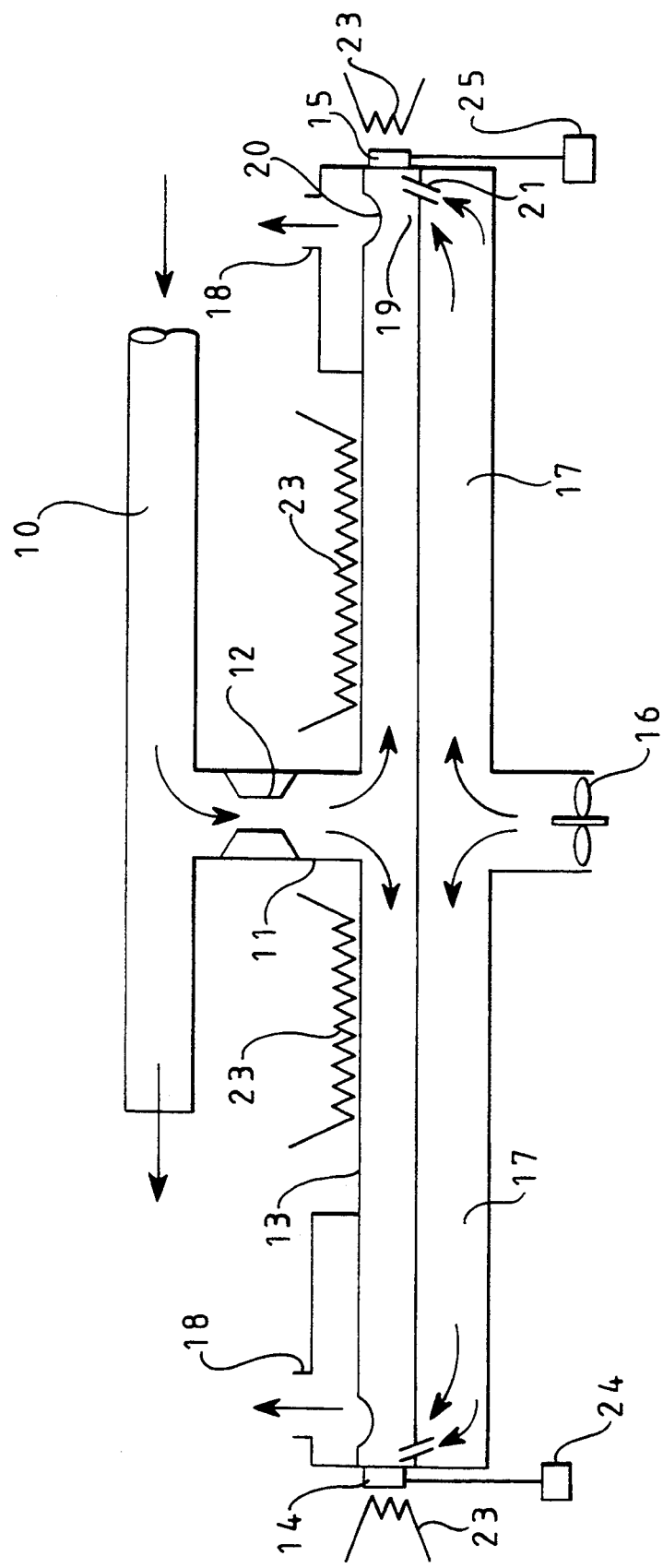

SMOKE METER

BACKGROUND OF THE INVENTION

1. Field of the Invention

This invention relates to smoke meters and, particular, to metering devices for determining the level of smoke content in, for example, the exhausts of road vehicles.

2. Description of the Art

The emission of quantities of smoke from vehicle engines has become environmentally unacceptable. In order to control the level of smoke emission it is necessary to obtain some indication as to the quantity of smoke being emitted. Such metering is necessary before any control can be exercised over vehicles which emit too much smoke.

The elements in the exhaust emissions which the present application addresses include carbon particles and other particulate material which may be present. The presence of water particles is not normally of particular concern and there are other means for determining the presence of noxious gases.

In metering the levels of smoke in vehicle emissions it has been proposed to pass a light beam through a sample of exhaust gas and to detect the amount of light which is able to be transmitted from the light source to a light detector. However, deposits of materials from the smoke sample on the surfaces of the light emitting and the light detecting means can affect the amount of light passing through the sample and one object of the present invention is to reduce such deposition.

In British Patent Specification No. 1135146 and in European Patent Specification No. 0456202 there are described smoke meters in which an attempt has been made to keep optical surfaces clear of deposits by using air flows. In European Patent 370248 deposits on the optical surfaces are burned off.

SUMMARY OF THE INVENTION

An object of the invention is to provide an improved smoke meter.

According to the invention a smoke meter comprises a measuring tube communicating with a source of smoke laden gas to be sampled, light emitting means at one end of the tube, light detecting means remote from the light emitting means for detecting light from the light emitting means passing through the gas, air flow generating means, air flow guidance means communicating between the air flow generating means and the measuring tube, air inlet means for admitting air from the air flow guidance means into the tube adjacent the light emitting means and the light detection means to pass over the light detection and the light emitting means and inhibit the deposition of smoke content on such means, and outlet means for discharging the gas and the air from the tube, such discharge being induced by air flow in the air flow guidance means.

Preferably the meter comprises openings in the measuring tube adjacent each of the light emitting means and the light detection means, air being admitted to the tube at one of the openings constituting the air inlet means and discharged through another of the openings constituting the discharge means, the openings lying at different sides of the tube.

Conveniently each discharge opening is arranged to discharge smoke laden gas with the air and has a larger size than the air inlet openings. The air inlet opening is upstream in the air flow passing along the air guidance means in relation to the outlet opening. The air flow guidance means passes around the openings and the tube, thereby inducing the flow of smoke laden gas along the tube. By careful regulation of the size of the openings, entry of air into the measuring tube can be made to be adequate to keep the light emitting means and the light detection means substantially clear of smoke deposits.

The arrangement is such that air is caused to flow at increased velocity in the vicinity of the openings to induce a flow of gas into the tube. Rapid meter response is possible and gas is rapidly purged from the measuring tube at the end of a test. The air flow generating means is located such that it passes clear air to the air guidance means and does not become contaminated with smoke laden gas.

By careful arrangement of the sizes and positions of the openings the induced flow of gas and air is provided. The pressure within the tube can be controlled to within 10 millibar of the ambient pressure even when the pressure of exhaust gas from a vehicle is considerably higher than the ambient pressure. This ensures that accurate and consistent measurements of smoke content can be achieved.

Preferably the smoke meter samples a portion of the total gas flow by providing an inlet opening from the main gas flow into the measuring tube. The size of the sample may be determined by constriction means and by the provision and arrangement of the air flow generating means.

Preferably the measuring tube is maintained in a heated condition by heating means to prevent condensation of water vapor and volatile hydrocarbons in the tube. Moreover, the entry of the sample may be located intermediate the ends of the sampling tube for passage towards its opposite ends.

Conveniently the light emitting means comprises a pulsed light source whereby intermittent pulses of light are directed towards the light detection means, the meter comprising means by which selected light pulses are suppressed or ignored.

BRIEF DESCRIPTION OF THE DRAWING

Further features of the invention will appear from the following description of an embodiment of the invention given by way of example only and with reference to the accompanying drawing which shows, schematically, a smoke meter.

DESCRIPTION OF THE PREFERRED EMBODIMENT

Referring now to the drawing, a gas sample for metering is passed along a sampling pipe 10 from a source of gas such as a vehicle engine exhaust. Part way along the pipe 10 is located a tube 11 having an optional constriction 12 to inhibit the bulk of the gas passing along the pipe 10 from entering the tube 11. The tube 11 communicates with a measuring tube 13 midway between the ends of the tube 13.

At opposite ends of the tube 13 there are located a light emitting device 14 and a light detection device 15. In use, light is emitted by the light emitting device 14 and is directed towards the light detection device 15. It is intended that the amount of light detected by the light detection device 15 be dependent on the smoke content of the sample entering the tube 13.

A fan 16 provides a supply of clean atmospheric air which is passed into an air guidance duct 17 extending towards and around the opposite ends of the tube 13. The air is guided to pass through and around the ends of the tube 13, as shown by the arrows. The openings in the ends of the tube 13 are arranged to admit air from the duct 17 into the tube 13 and also to allow air and the gas sample in the tube 13 to pass to discharge outlets 18 of the duct 17. Thus, the openings at each end of the tube 13 include an outlet opening 20 together with an inlet opening 21 to provide flushing or purging air for the light emitting device 14 at one end of the tube and for the light detection device 15 at the other end of the tube 13. The cross-sectional areas of each of the openings 20 and 21 are carefully arranged to induce the entry of air into the tube 13 through the opening 21 while allowing the gas and air to be discharged from the opening 20 by a venturi action. The opening 20 may be replaced by two openings on diametrically opposite sides of the tube 13 with the air flow around the tube 13 arranged to have minimal contact with the tube 13 to reduce cooling of the tube 13.

The outlet opening 20 or openings are generally circular and lie towards the downstream side of the tube 13 in each case. The inlet openings 21 may each comprise a short inlet tube communicating with the duct 17 at the upstream side of the tube 13 and directed across the face of the associated light emitting device 14 or light detection device 15 whereby a stream of clean air from the duct 17 passes across the face of device 14 or 15 to prevent or inhibit the deposition of materials from the sample on such face. It has been found by careful control of the sizes of the openings 20 and 21 that deposition on the faces of the devices 14 and 15 can be substantially eliminated. It will be appreciated that clear air passing along the duct 17 passes around the tube 13 at its ends in addition to passing into the tube 13 through openings 20 and 21.

In order to prevent condensation of the water content of the sample the tube 13 is heated by heating elements 23 disposed to heat the tube 13 and the light emitting and detection devices 14 and 15 to, for example, 70 degrees Centigrade.

It will be appreciated that the quantity of smoke sample passing from the outlets 18 is small and is mixed with clear air supplied by the fan 16.

Conventionally, smoke meters are calibrated by introducing mechanically a translucent filter which can obscure a known percentage of the light or by an opaque screen which will obscure a known percentage of the light beam. Such devices cause complications in the mechanisms for allowing their entry and extraction.

The smoke meter is arranged to avoid these complications by making use of a pulsed or intermittent light source. By suppressing alternate pulses of light an accurate 50% total light signal can be obtained and when a light detection device is provided with linear detection characteristics, a simple, convenient calibration point can be established without mechanical intervention. Instead of suppressing alternate pulses of light two out of three, three out of four pulses or other ratios of light pulses may be suppressed. Instead of suppression of pulses of light the detection means may be arranged to detect only selected pulses of light ignoring alternate or other pulses. The pulsed light source may be generated in any convenient means or the pulses can be generated mechanically by shutter or other means interposed in the light path.

The device described above is of relatively simple construction arranged to keep the light path free of smoke deposits and to sample a significant quantity of gas by splitting the original sample along two paths and by providing a measuring tube 13 of adequate length which may be of the order of 250 mm in a tube having a diameter of the order of 17 min. Moreover, the pressure differential across the device may be of the order of 10 millibars. The outlet openings 20 may be of the order of 10 mm in diameter.

The arrangement also results in the measuring tube 13 being purged of sample once the device is disconnected from the exhaust being sampled or the supply of gas to the tube 10 is otherwise interrupted.

Instead of the light emitting device 14 and the light detection device 15 being at opposite ends of the tube 13 they may be at the same end with means for deflecting the light beam from one to the other.

I claim:

1. A smoke meter comprising a measuring tube communicating with a source of smoke laden gas to be sampled, light emitting means disposed at one end of the tube, light detection means remote from the light emitting means for detecting light from the light emitting means passing through the gas, air flow generating means for generating an air flow, air flow guidance means communicating between the air flow generating means and the measuring tube for guiding the air flow to the measuring tube, air flow inlet means defined by first openings in the measuring tube for admitting air from the air flow guidance means into the measuring tube adjacent each of the light emitting means and the light detection means to pass the admitted air over the light detection and the light emitting means and to inhibit the deposition of smoke content on the light detection and light emitting means, and outlet means defined by further openings in the measuring tube for discharging the gas and the air from the measuring tube, said first and further openings lying at different sides of the tube, wherein said further outlet openings have a larger size than said first inlet openings, said first openings being upstream from said further openings with regard to the air flow passing along the air guidance means, the air guidance means extending around said first and further openings and around the measuring tube to permit an air flow around said first and further openings and around the measuring tube, to thereby induce a flow of smoke laden gas along the measuring tube for discharge through said further openings.

2. The smoke meter according to claim 1 wherein the light emitting means and the light detection means are at opposite ends of the measuring tube and the meter comprises an inlet for introducing the smoke laden gas into the measuring tube, the inlet being disposed at a position along the measuring tube intermediate the light emitting means and the light detection means, the smoke laden gas passing from the inlet towards the light emitting means and the light detection means.

3. The smoke meter according to claim 1 wherein the measuring tube communicates with a duct arranged to selectively communicate with said source of smoke laden air or with a source of atmospheric air by which a sample of the smoke laden gas is caused to flow from the duct into the measuring tube during a measuring operation and the flow of gas is replaced with a flow of air for purging of the gas from the measuring tube, the flows of gas and air being induced by a venturi effect of air flow in the air flow guidance means.

4. The smoke meter according to claim 1 further comprising heating means for heating the measuring tube to prevent the deposition of contents of the smoke laden air on the measuring tube.

5. The smoke meter according to claim 1 wherein the light emitting means comprises a pulsed light source whereby intermittent pulses of light are directed towards the light detection means, and in order to calibrate the meter there is provided means by which selected light pulses are suppressed or ignored at the light emitting or the light detection means.

6. A smoke meter comprising a measuring tube communicating with a source of smoke laden gas to be sampled, light emitting means disposed at one end of the tube, light detection means remote from the light emitting means for detecting light from the light emitting means passing through the gas, air flow generating means for generating an air flow, air flow guidance means communicating between the air flow generating means and the measuring tube for guiding the air flow to the measuring tube, air flow inlet means defined by first openings in the measuring tube for admitting air from the air flow guidance means into the measuring tube adjacent each of the light emitting means and the light detection means to pass the admitted air over the light detection and the light emitting means and to inhibit the deposition of smoke content on the light detection and light emitting means, and outlet means defined by further openings in the measuring tube for discharging the gas and the air from the measuring tube, said first and further openings lying at different sides of the tube, wherein said further outlet openings have a larger size than said first inlet openings, said first openings being upstream from said further openings with regard to the air flow passing along the air guidance means, the air guidance means extending around said first and further openings and around the measuring tube to permit an air flow around said first and further openings and around the measuring tube, to thereby induce a flow of smoke laden gas along the measuring tube for discharge through said further openings, and wherein the measuring tube communicates with a supply duct arranged to selectively communicate with said source of smoke laden gas or with a source of atmospheric air, a sample of said smoke laden gas being supplied from said gas source to said duct and into the measuring tube during a measuring operation, and the source of air being supplied to said duct and into the measuring tube in order to purge the gas from the measuring tube, the flow of gas or air from said source being induced by a venturi effect caused by the air flow in the air guidance means over said first and further openings.

7. A smoke meter comprising a measuring tube communicating with a source of smoke laden gas to be sampled, light emitting means disposed at one end of the tube, light detection means at the other end of the tube for detecting light from the light emitting means passing through said gas, air flow generating means for generating an air flow, air flow guidance means communicating between the air flow generating means and the measuring tube for guiding the air flow to the measuring tube, air inlet means for emitting air from the air flow guidance means into the measuring tube adjacent each of the light emitting means and the light detection means and to inhibit the deposition of smoke contents on the light detection and light emitting means, and outlet means for discharging the gas and the air from the measuring tube, the discharge being induced by the air flow in the air flow generating means, wherein the light emitting means comprises a pulsed light source whereby intermittent pulses of light are directed towards the light detection means and in order to calibrate the meter, there is provided means by which selected light pulses are suppressed at the light emitting or light detection means.

* * * * *

UNITED STATES PATENT AND TRADEMARK OFFICE
CERTIFICATE OF CORRECTION

PATENT NO. : 5,353,629
DATED : October 11, 1994
INVENTOR(S) : Colin Hunter

It is certified that error appears in the above-indentified patent and that said Letters Patent is hereby corrected as shown below:

Column 3, line 55, after "source" please insert --utilizing pulsing means 24--.

Column 3, line 65, after "pulses" please insert --utilizing pulse detection means 25--.

Column 4, line 7, after "17" please delete "min" and insert --mm--.

Signed and Sealed this

Twenty-eight Day of February, 1995

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,353,629
DATED : October 11, 1994
INVENTOR(S) : Colin Hunter

It is certified that error appears in the above-indentified patent and that said Letters Patent is hereby corrected as shown below:

On the title page, item [73]

Assignee: please delete "L.L." and insert --V.L.--.

Signed and Sealed this

Twenty-third Day of May, 1995

Attest:

BRUCE LEHMAN

*Attesting Officer*     *Commissioner of Patents and Trademarks*